US010729394B1

(12) United States Patent
Foos et al.

(10) Patent No.: US 10,729,394 B1
(45) Date of Patent: Aug. 4, 2020

(54) PORTABLE SCANNING SYSTEM FOR IMAGING PATIENTS

(71) Applicant: CARESTREAM HEALTH, INC., Rochester, NY (US)

(72) Inventors: David H. Foos, Webster, NY (US); Samuel Richard, Rochester, NY (US); Timothy J. Wojcik, Rochester, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 4 days.

(21) Appl. No.: 16/037,341

(22) Filed: Jul. 17, 2018

Related U.S. Application Data

(60) Provisional application No. 62/533,699, filed on Jul. 18, 2017.

(51) Int. Cl.
*A61B 6/00* (2006.01)
*A61B 6/06* (2006.01)

(52) U.S. Cl.
CPC .............. *A61B 6/4233* (2013.01); *A61B 6/06* (2013.01); *A61B 6/4405* (2013.01); *A61B 6/587* (2013.01); *A61B 6/465* (2013.01); *A61B 6/588* (2013.01)

(58) Field of Classification Search
CPC ................................ A61B 6/06; A61B 6/4405
See application file for complete search history.

(56) References Cited

U.S. PATENT DOCUMENTS

| | | | | |
|---|---|---|---|---|
| 7,286,636 | B2 | 10/2007 | Unger et al. | |
| 7,564,938 | B2 | 7/2009 | Tesic et al. | |
| 8,821,015 | B2 | 9/2014 | Stagnitto et al. | |
| 2004/0213380 | A1* | 10/2004 | Shaw | A61B 6/06 378/145 |
| 2006/0104415 | A1 | 5/2006 | Unger et al. | |
| 2009/0086926 | A1* | 4/2009 | Wang | A61B 6/4405 378/206 |

FOREIGN PATENT DOCUMENTS

| | | |
|---|---|---|
| EP | 0 182 529 | 5/1986 |
| WO | 2014/081686 | 5/2014 |

* cited by examiner

*Primary Examiner* — Dani Fox

(57) ABSTRACT

A slot scanning system and method for imaging a patient. The method comprises: providing a source of x-ray radiation, directed toward a subject; providing a large flat portable freely-positionable non-tethered stationary digital detector spaced from the source and positioned to receive the x-ray radiation; providing a slotted collimator intermediate the x-ray source and digital detector; and generating a digital x-ray image of the patient by combining a captured plurality of line images.

5 Claims, 8 Drawing Sheets

Last Position

PORTABLE SCANNING SYSTEM FOR IMAGING PATIENTS

CROSS REFERENCE TO RELATED APPLICATIONS

This application claims priority to U.S. Provisional application U.S. Ser. No. 62/533,699, provisionally filed on Jul. 18, 2017, entitled "PORTABLE SCANNING SYSTEM FOR IMAGING PATIENTS", in the names of Foos et al, incorporated herein in its entirety.

TECHNICAL FIELD

The disclosure relates generally to the field of imaging, and in particular to medical imaging More specifically, the disclosure relates to a portable slot scanning system for imaging patients, particularly, bariatric ICU patients.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

Figure 1:
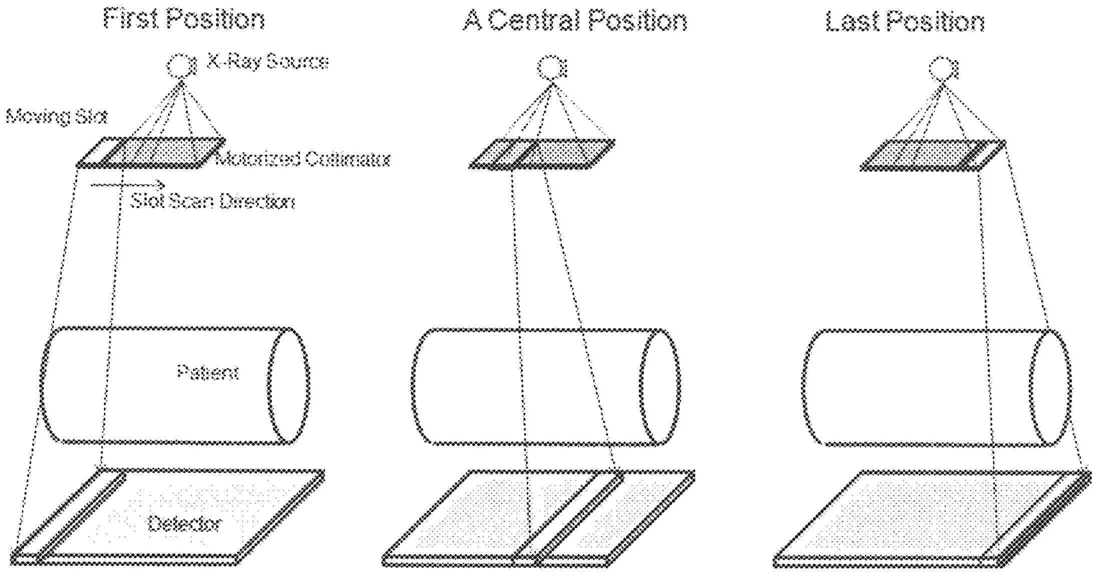
FIG. 1 shows a portable slot scanning system for imaging patients, according to the present disclosure.

The following is a detailed description of the preferred embodiments, reference being made to the drawings in which the same reference numerals identify the same elements of structure in each of the several figures.

Slot scanning systems are known, for example. Slot (or slit) scanning imaging techniques using collimated x-ray beams have been developed. With such a system, a narrow collimated x-ray beam is used. Reference is made to US 2004/0213380 (Shaw), U.S. Pat. No. 7,564,938 (Tesic), and EP 0182529 (Sones), incorporated herein in their entirety.

Reference is made to US 2006/0104415 (Unger) and U.S. Pat. No. 7,286,636 (Unger) directed to a flat panel detector based slot scanning configuration, incorporated herein in their entirety.

Applicants have developed a portable DR (digital radiography) system configured with a slot scanning tube head and a large flat FOV (field of view) (e.g., 43 cm×43 cm) DR detector, preferably having a high frame rate and capability to sequentially read out specified contiguous series of rows or columns (e.g., bands of image data).

Referring to the figures, there is shown a radiographic imaging scanner system/apparatus comprising:

(i) a source of x-ray radiation, directed through a portion of a subject;

(ii) a large flat portable freely-positionable non-tethered stationary digital detector spaced from the source and positioned to receive the radiation;

(iii) a slotted device/collimator, positioned intermediate the x-ray source and digital detector, and mounted for translational movement in a plane substantially parallel to the digital detector; and (iv) means for producing an image representing the received radiation.

The disclosed apparatus and method is adapted to perform a high frame rate imaging, for example: fluoroscopy and tomosynthesis imaging.

Referring to the figures, there is shown a slot scanning method for imaging patients. A source of x-ray radiation is provided, and is directed toward a subject/patient.

As illustrated, there is provided a large flat portable freely-positionable non-tethered stationary digital detector spaced from the source and positioned to receive the x-ray radiation. An example of a suitable large flat portable freely-positionable non-tethered stationary digital detector is the DRX detectors available from Carestream Health, Inc. In a preferred arrangement, the high frame rate and large FOV DR detector provide low exposure detective quantum efficiency (DQE).

A slotted collimator is disposed intermediate the x-ray source and digital detector. In a preferred arrangement, the dimensions of the slot are configurable to direct the x-ray radiation to impinge the digital detector in a slot/linear manner.

Figure 2:
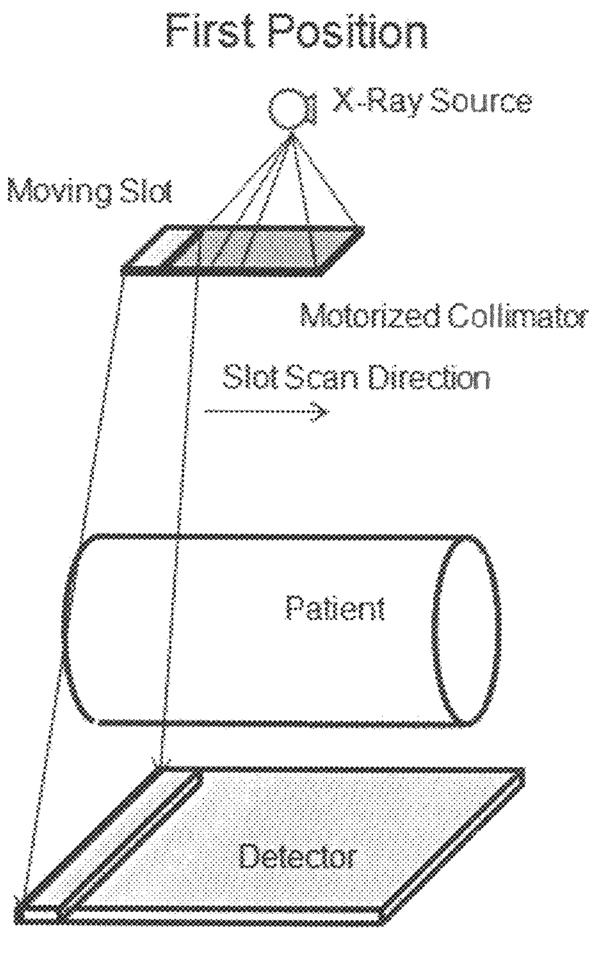
FIGS. 2-5 show further illustrations of the system of FIG. 1.
Figure 3:
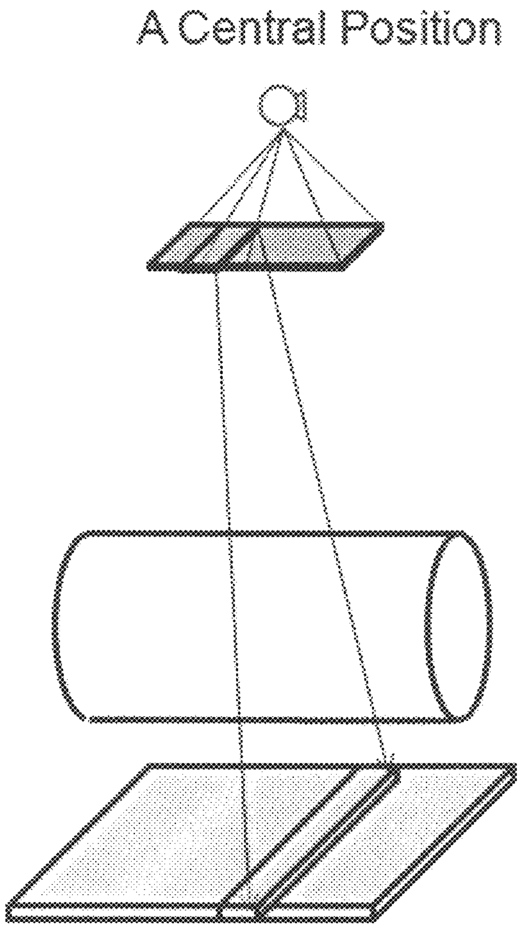
Figure 4:
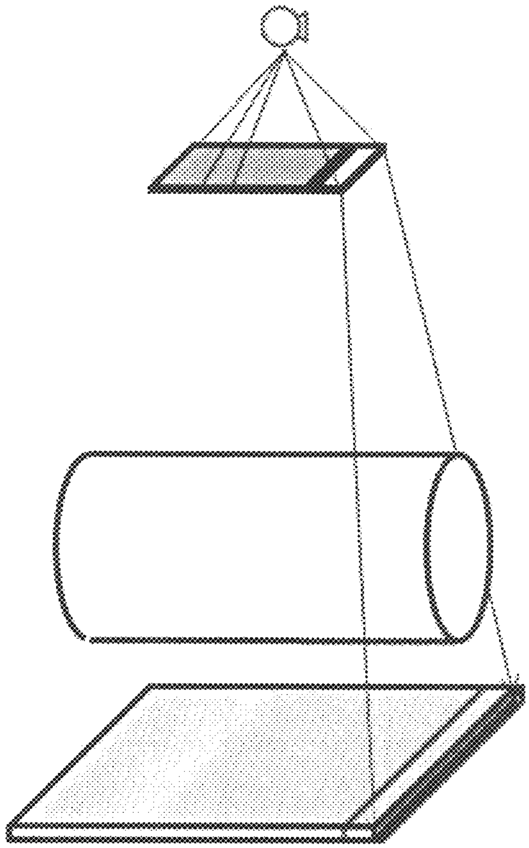
Figure 5:
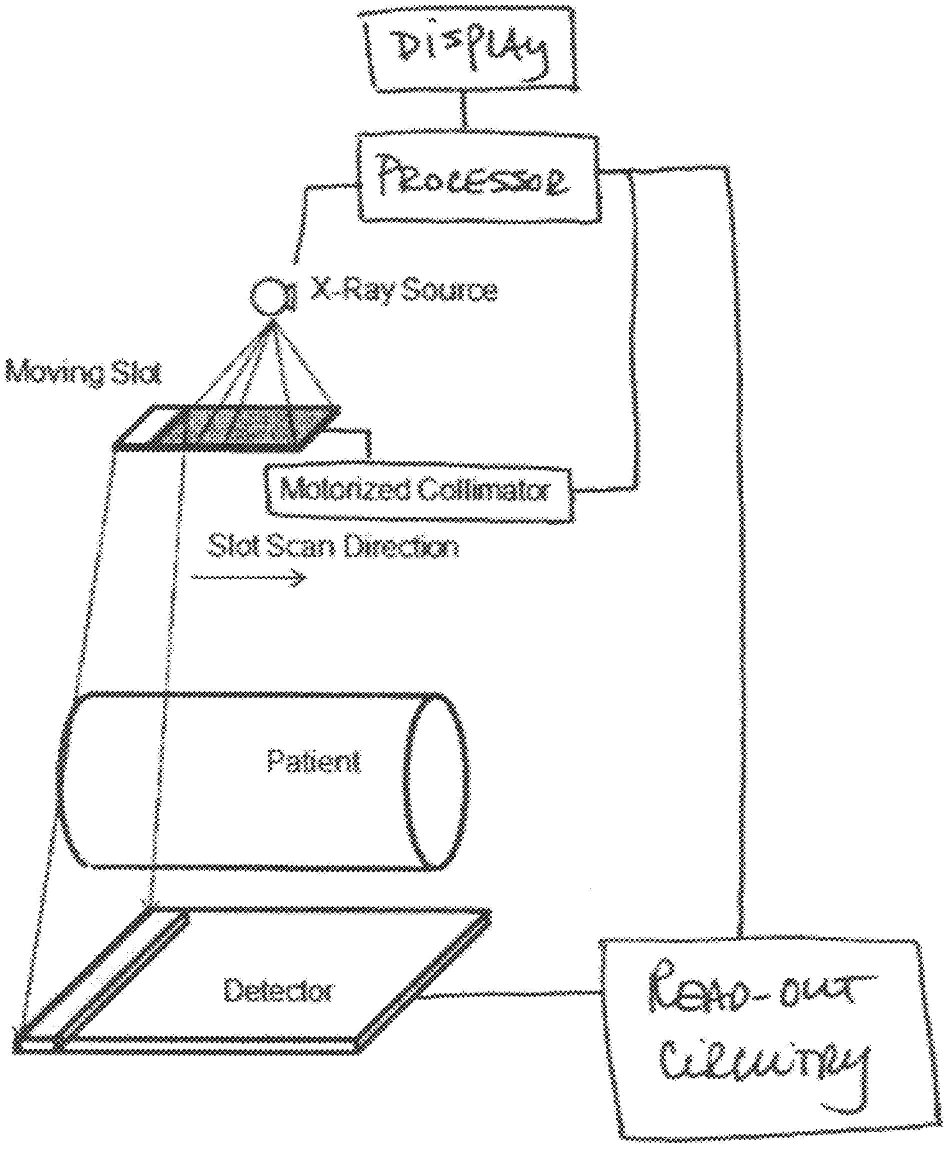

As best illustrated in FIG. 1, to capture a digital x-ray image, the slotted collimator is positioned in a first position relative to the digital detector and the x-ray radiation is directed through the slotted collimator to impinge the digital detector, wherein the readout circuitry generates a digital line image. Thereafter, the slotted collimator is translated in a plane substantially parallel to the digital detector to a second/another position, such as illustrated in FIG. 2, and again the x-ray radiation is directed through the slotted collimator to impinge the digital detector, wherein the readout circuitry generates another/second digital line image. Thereafter, the slotted collimator is further translated in a plane substantially parallel to the digital detector to a third/another position, such as illustrated in FIG. 3, where the x-ray radiation is directed through the slotted collimator to impinge the digital detector, wherein the readout circuitry generates another/third digital line image. This process is repeated until the desired number of digital line images is captured.

Once the digital line images have been captured, the captured images can processed to generate a digital image of the subject. This processing can be accomplished by stitching the line images (if a pulsed x-ray radiation beam was employed, i.e., step/shot) or by the addition of the line images (if a continuous radiation beam was employed).

The generated digital image of the subject can be stored, transmitted, or displayed.

A processor is used to control the operation and various functions of the apparatus.

Since the detector is freely-positionable, it may be desirable to improve the alignment of the source to the detector. An example of a suitable alignment aid apparatus is disclosed in U.S. Pat. No. 8,821,015 (Stagnitto) titled ALIGNMENT APPARATUS FOR X-RAY IMAGING SYSTEM, incorporated herein in its entirety.

In a preferred arrangement, the detector is a large flat portable non-tethered stationary digital detector.

In a preferred arrangement, the source is a source of pulsed x-ray radiation.

In a preferred arrangement, the system includes a tube head with a motorized collimator, where the collimation is configured as a slot that moves/translates sequentially across the FOV (field of view) of the stationary detector, either continuously or in a step and shoot manner.

Those skilled in the art recognize the mechanisms/apparatus available to mechanically translate the collimator in substantially planar motion parallel to the digital detector. Linear motion can be accomplished using a linear guide.

In an alternate embodiment, the system can employ a moving shutter as an alternate to a moving x-ray tube.

In a preferred arrangement, the system is capable of reading out a specified plurality of contiguous lines or rows of image data corresponding to the position of the collimated x-rays projected onto the detector.

In a preferred arrangement, the system includes a pulsed X-ray source/generator.

The system includes a processor for image processing to assemble a full composite image.

The system provides image quality, including scatter rejection without the need for an anti-scatter grid.

The system provides image quality, including lower patient dose. The scatter is minimized at the source (collimated), i.e., minimized skin entrance dose, in comparison to an anti-scatter grid which preferentially reduces the transmission of the scattered X-rays exiting the patient.

In an alternate embodiment, to improve image quality, a second slot would be employed. This second slot can be disposed (1) intermediate the x-ray source and patient, or (2) intermediate the patient and digital detector.

Figure 6:
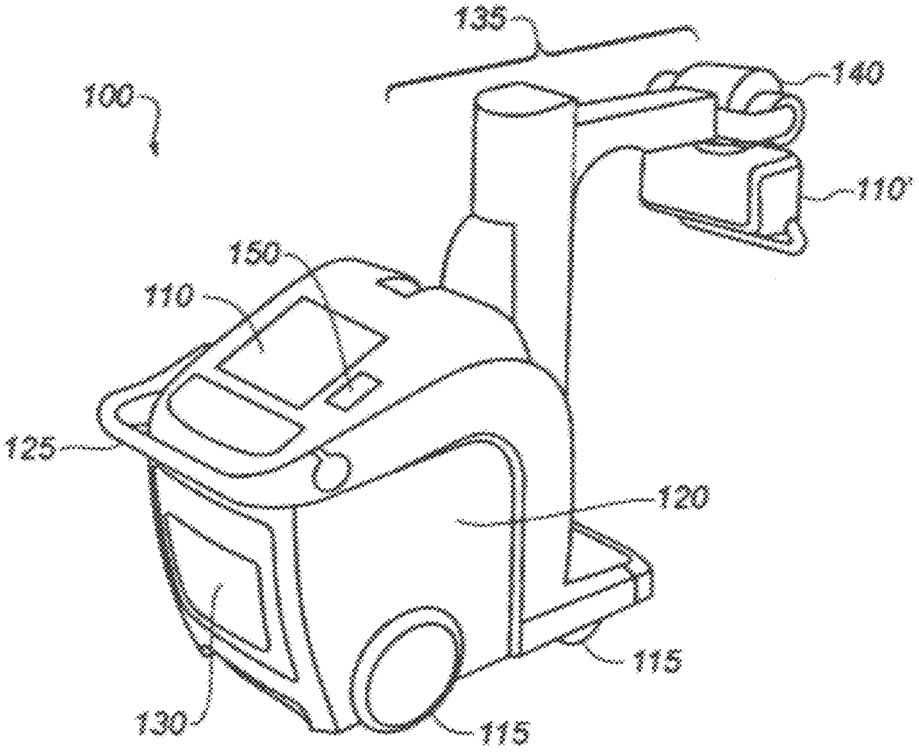
FIGS. 6-8 show illustrations of a collimator system.

FIG. 6 is a diagram that shows a perspective view of a mobile radiography unit having an x-ray source suitable for the disclosed method. In addition, the unit can be used to mount/move/translate the slotted collimator.

As shown in the figure, a mobile radiography apparatus 100 can include a moveable transport frame 120 that includes a first display 110 and an optional second display 110' for display relevant information such as obtained images and related data. As shown in the figure, the second display 110' can be pivotable mounted at the x-ray source 140 to be viewable/touchable from a 360 degree area.

The displays 110, 110' can implement or control (e.g., touch screens) functions such as generating, storing, transmitting, modifying, and printing of an obtained image(s) and can include an integral or separate control panel (not shown) to assist in implementing functions such as generating, storing, transmitting, modifying, and printing of an obtained image(s).

For mobility, the mobile radiographic apparatus 100 can have one or more wheels 115 and one or more handle grips 125, typically provided at waist-level, arm-level, or hand-level, that help to guide the mobile radiographic apparatus 100 to its intended location. A self-contained battery pack (e.g., rechargeable) in the frame or elsewhere can provide source power, which can reduce or eliminate the need for operation near a power outlet. Further, the self-contained battery pack can provide for motorized transport.

For storage, the mobile radiographic apparatus 100 can include an area/holder for holding/storing one or more digital radiographic (DR) detectors or computed radiography (stimulated phosphor) cassettes. The area/holder can be storage area 130 (e.g., disposed on the frame 120) configured to removably retain at least one digital radiography (DR) detector. The storage area 130 can be configured to hold a plurality of detectors and can also be configured to hold one size or multiple sizes of DR detectors or cassettes.

Mounted to frame 120 is a support column 135 that supports an x-ray source 140, also called an x-ray tube, tube head, or generator that can be mounted to the support member 135. In the embodiment shown in FIG. 6, the support member (e.g., column 135) can include a second section that extends outward a fixed/variable distance from a first section where the second section is configured to ride vertically up and down the first section to the desired height for obtaining the image. In another embodiment, the tube head or x-ray source 140 can be rotatably coupled to the support column 135. In another exemplary embodiment, an articulated member of the support column that bends at a joint mechanism can allow movement of the x-ray source 140 over a range of vertical and horizontal positions. Height settings for the x-ray source 140 can range from low height for imaging feet and lower extremities to shoulder height and above for imaging the upper body portions of patients in various positions. The mobile radiographic apparatus 100 can also include a prep/expose control 150.

Figure 7:
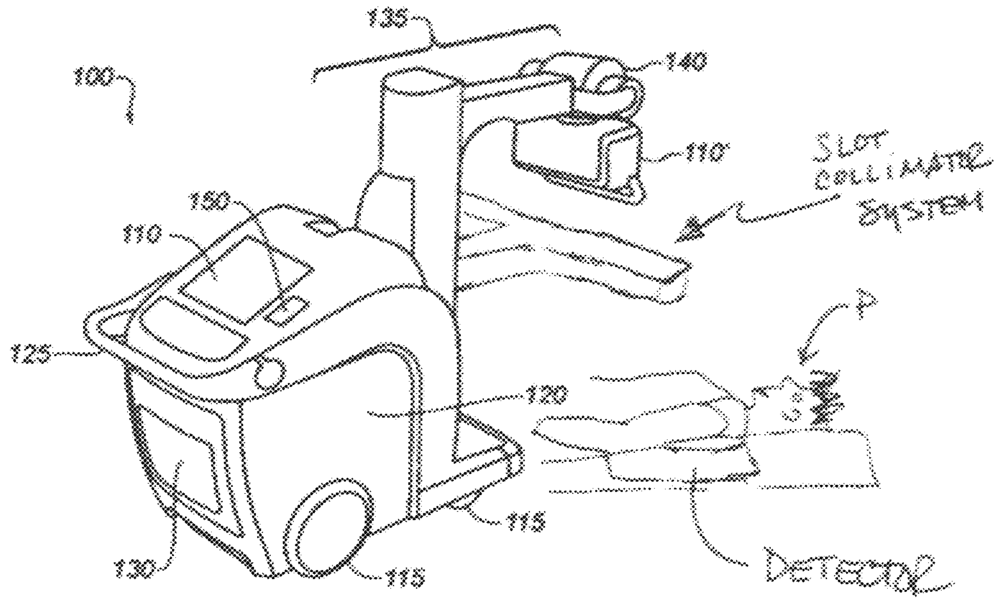
Figure 8:
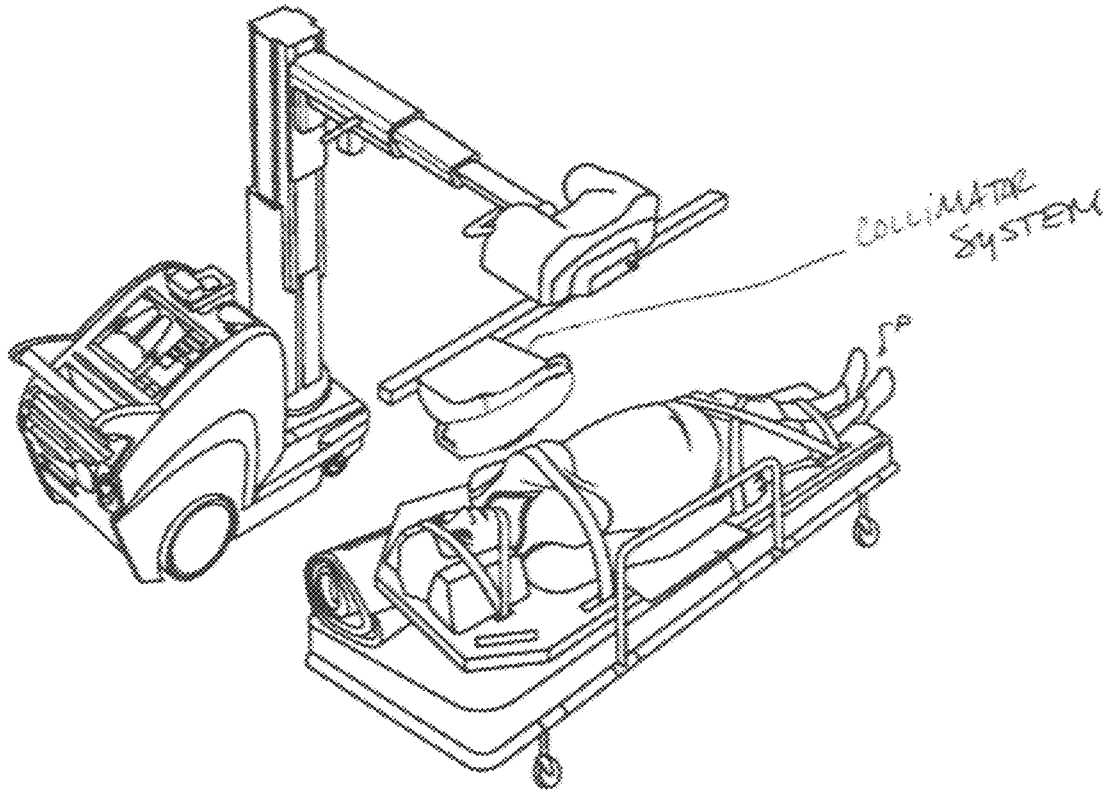

Referring to FIGS. 7 and 8, a slotted collimator system (comprising the slotted collimator) can be mounted to column 135 or to frame 120, such that the slotted collimator translates in a planar path substantially parallel to the digital detector. If mounted to the x-ray tube head, the translation can be described as being in a plane/line substantially perpendicular to the x-ray source, wherein in operation the tube head would preferably be positioned substantially perpendicular to the digital detector. Reference is made to WO 2014/081686 (Simon) titled SCAN GEOMETRY CORRECTIONS FOR TOMOSYNTHESIS MOBILE RADIOGRAPHIC APPARATUS, incorporated herein in its entirety by reference.

The power from the mobile radiography apparatus 100 can be used to power the slotted collimator system.

The disclosed system combines slot scanning with portable digital radiography, which is particularly suited for bedside imaging of bariatric patients where there is a benefit to the patient of reduced x-ray scatter. As such, in a preferred arrangement, the system provides image quality, including optimal design for portable DR imaging of bariatric patients, including patients in the intensive care unit (ICU). The system can additionally produce optimal images for any sized patient.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A slot scanning system for imaging a patient, the system comprising:

a moveable transport frame having wheels for rollably moving the slot scanning system;

a support member mounted to the transport frame, the support member comprising a first section and a second section that extends outward a variable distance from the first section;

a tube head mounted to the second section, the tube head comprising a source of x-ray radiation, directed toward a subject;

a flat portable freely-positionable digital detector spaced from the source of x-ray radiation and positioned to receive the x-ray radiation;

a slotted collimator attached to the support member and disposed intermediate the x-ray source and the digital detector, the slotted collimator configured to translate to a plurality of imaging positions in a plane substantially parallel to a plane of the digital detector; and a processor for generating a digital x-ray image by combining a plurality of a digital line images captured by the digital detector at each of the plurality of imaging positions.

2. The slot scanning system of claim 1, wherein the source of x-ray radiation is configured to emit pulsed radiation.

3. The slot scanning system of claim 1, wherein the source of x-ray radiation is configured to emit a continuous beam of radiation.

4. The slot scanning system of claim 1, further comprising a display for displaying the generated digital x-ray image.

5. The slot scanning system of claim 1, further comprising an alignment aid configured to facilitate aligning the x-ray source and the digital detector.

* * * * *